United States Patent [19]

Reed

[11] Patent Number: 5,413,912
[45] Date of Patent: May 9, 1995

[54] PEPTIDE FOR DETECTING ANTIBODIES TO A 260 KD T. CRUZI ANTIGEN

[76] Inventor: Steven G. Reed, 2843-122nd Pl. NE., Bellevue, Wash. 98005

[21] Appl. No.: 169,563

[22] Filed: Dec. 17, 1993

Related U.S. Application Data

[62] Division of Ser. No. 836,642, Feb. 14, 1992, Pat. No. 5,304,371.

[51] Int. Cl.$^6$ .......................................... G01N 33/569
[52] U.S. Cl. ................... 435/7.22; 435/7.92; 435/7.94; 435/975; 436/518; 436/532
[58] Field of Search ............ 435/7.22, 7.92, 7.94, 435/975; 436/518, 513, 811, 828, 532; 530/387.9, 388.6

[56] References Cited

PUBLICATIONS

Ibanez et al., *Mol. Biochem. Parasit.* 25:175–184; 1987.
Ibanez et al., *Mol. Biochem. Parasit.* 30:27–34; 1988.
Affranchino et al., *Mol. Biochem. Parasit.* 34:211–228; 1989.
Frasch and Reyes, *Parasit. Today* 6:137–139; 1990.
Hoft et al., *Inf. and Immun.* 57:1959–1967; 1989.
Vergara et al., *J. Clin. Microbiol.* 29:2034–2037; 1991.
Peterson et al., *Nature* 322:566–567; 1986.
Reed, Annual Meeting of the American Society of Tropical Medicine and Hygiene, round table presentation; Nov. 1990.
Martinez et al., *Infection and Immunity*, 59:4275–4277; 1991.
Mitchell, "Vaccines and Vaccination Strategy," in *Parasitology*; 1989; pp. 519–528.
Burns et al, "Identification and Synthesis of a Major Conserved Antigenic Epitope of *Trypanosoma cruzi*", *Proc. Natl. Acad. Sci. USA*, 8(4):1239–1243 (Feb. 15, 1992).

*Primary Examiner*—Carol E. Bidwell
*Attorney, Agent, or Firm*—Patricia Anne Perkins; Jeffrey R. Oster

[57] ABSTRACT

There is disclosed an antigenic peptide that comprises at least 15 amino acids having the sequence Ala Glu Pro Lys X Ala Glu Pro Lys X Ala Glu Pro Lys X, wherein X is Pro or Ser. This peptide is useful in an ELISA assay to detect antibodies specific to *T. cruzi* infection and Chagas disease. This peptide is further useful in a vaccine composition for immunizing an individual to prevent Chagas disease upon exposure to *T. cruzi*.

13 Claims, 2 Drawing Sheets

```
1                                                                                                                                    GAATTCA
8    GCA GAG CCC AAA CCA GCG GAG CCT AAA CCA GCG GAG CCG AAA CCA GCG GAG CCG AAA TCG
     ALA GLU PRO LYS PRO ALA GLU PRO LYS PRO ALA GLU PRO LYS PRO ALA GLU PRO LYS SER
68   GCA GAG CCC AAA CCA GCG GAG CCC AAA CCG GAG CCG AAA CCA GCG GAG CCG AAA TCA
     ALA GLU PRO LYS PRO ALA GLU PRO LYS PRO GLY PRO LYS PRO ALA GLU PRO LYS SER
128  GCG GGG CCT AAA CCA GCG GAG CCG AAA CCA GCG GAG CCG AAA TCA
     ALA GLY PRO LYS PRO ALA GLU PRO LYS PRO ALA GLU PRO LYS SER
188  GCA GAG CCC AAA CCA GCG GAG CCG AAA CCG GAG CCG AAA CCA GCG GAG CCG AAA TCA
     ALA GLU PRO LYS PRO ALA GLU PRO LYS PRO GLY PRO LYS PRO ALA GLU PRO LYS SER
248  GCA GAG CCC AAA CCA GCG GAG TCG AAG TCA GCA GAG CCT AAA CCA GCG GAG CCG AAA TCA
     ALA GLU PRO LYS PRO ALA GLU SER LYS SER ALA GLU PRO LYS PRO ALA GLU PRO LYS SER
308  GCA GAG CCC AAA CCA GCG GAG TCG AAG TCA GCA GAG CCC AAA CCA GCG GAG CCG AAA TCA
     ALA GLU PRO LYS PRO ALA GLU SER LYS SER ALA GLU PRO LYS PRO ALA GLU PRO LYS SER
368  GCA GAG CCC AAA CCA GCG GAG CCG AAA TCA GCA GAG CCC AAA CCA GCG GAG CCG AAA TCA
     ALA GLU PRO LYS PRO ALA GLU PRO LYS SER ALA GLU PRO LYS PRO ALA GLU PRO LYS PRO
428  GCA GAG CCC AAA CCA GCG GAG CCG AAA TCA GCA GAG CCC AAA CCA GCG GAG CCG AAA TCA
     ALA GLU PRO LYS PRO ALA GLU PRO LYS SER ALA GLU PRO LYS PRO ALA GLU PRO LYS PRO
488  GCG GGG CCT AAA CCA GCG GAG CCG AAA CCG GAG CCA AAA CCA GCG GAG TCG AAA TCA
     ALA GLY PRO LYS PRO ALA GLU PRO LYS PRO GLY PRO LYS PRO ALA GLU SER LYS PRO
548  GCG GAG CCC AAA CCA GCG GAG CCG AAA TCG GCA GAG CCC AAA CCA GCG GAG CCG AAA TCA
     ALA GLU PRO LYS PRO ALA GLU PRO LYS PRO ALA GLU PRO LYS PRO ALA GLU PRO LYS PRO
608  GCA GAG CCA AAA CCA GCG GAG CCGAATTC
     ALA GLU PRO LYS PRO ALA GLU
```

FIGURE 1

PEPTIDE FOR DETECTING ANTIBODIES TO A 260 KD *T. CRUZI* ANTIGEN

This invention was supported in part through grant number NIH AI22726 from the National Institutes of Health. The U.S. Government, therefore, may have certain rights to this invention.

This is a division of U.S. application Ser. No. 07/836,642, filed Feb. 14, 1992, issued Apr. 19, 1994, as U.S. Pat. No. 5,304,371.

TECHNICAL FIELD OF THE INVENTION

The present invention relates to a 15 met peptide that is the epitope repeat sequence for a predominant antigen of *T. cruzi*. The inventive peptide is useful for diagnosing *T. cruzi* infection and for use in a vaccine to immunize an individual to reduce *T. cruzi* infection and clinical manifestations of Chagas disease.

BACKGROUND OF THE INVENTION

Chagas disease is one of the most important endemic problems in Central and South America, for which no definitive chemotherapeutic or immunological treatment is available. *Trypanosoma cruzi* (*T. cruzi*) is the agent of Chagas disease. Infection with a protozoan parasite *T. cruzi*, the causitive agent of Chagas disease, occurs in an estimated 18 million persons throughout Latin America and is a major cause of chronic heart disease. Immune responses after *T. cruzi* infection are particularly complex due to the biochemical diversity of multiple parasite strains and influence of host-genetic factors. The result is a wide diversity in clinical manifestations of Chagas disease and, in some cases, the disruption of immune regulation leading to immunosuppression: and/or development of autoimmunity. This parasite has a complex life cycle involving an epimastigote stage in the insect vector and two main stages in the mammalian host. One stage is present in blood (trypomastigote) and a second stage is intracellular (amastigote).

The acute phase of *T. cruzi* infection is often asymptomatic. The infection may remain quiescent for decades. Some patients may, however, develop a progressive chronic form of the disease with cardiac and/or digestive tract alterations. After the acute phase with parasitemia, parasite growth is usually controlled by the host and patients or animals enter into a chronic phase where few parasites are present in the blood.

Immune responses to protozoan infection are complex, involving both humoral and cell-mediated responses to an array of parasite antigens. Infection often involves multiple life cycle stages of these parasites, which adds to the diversity of antigens potentially important for the development of protective immunity. To examine the molecular basis of the immune responses elicited during these infections, recent efforts have focused on evaluating responses to defined parasite B- and T-cell epitopes.

*T. cruzi* infections are often subtle and long-lasting, making diagnosis crucial and problematic. Detecting antibodies against parasite antigens is a most common and reliable method of determining clinical and subclinical infections. Presently, serological tests use whole or lysed *T. cruzi* and require positive results on two of three tests, including complement fixation, indirect immunofluorescence, passive agglutination, or ELISA to accurately detect *T. cruzi* infection. The expense as well as difficulty in performing such tests reliably prevent the screening of blood or sera in many endemic areas.

Blood bank screening is particularly important in South America, where 0.1–62% of samples may be infected and where the parasite is frequently transmitted by blood transfusion. It is also important and of increasing concern that the blood supply in certain U.S. cities is contaminated with *T. cruzi* parasites.

Therefore, there is a need in the an for a greater understanding of responses to specific parasite antigens. Although several antigens of *T. cruzi* have been identified and characterized biochemically, limited data are available on the evaluation of human immune responses to these molecules.

SUMMARY OF THE INVENTION

The present invention relates to the cloning and expression of a *T. cruzi* antigen gene sequence (SEQ ID NOs: 1 and 2) encoding the immunodominant protein with an essential repetitive epitope. This gene sequence is conserved among diverse *T. cruzi* isolates. The inventive antigenic peptide domain of *T. cruzi* is predominantly expressed by trypomastigotes, the infective form of the parasite. Evaluation of human immune responses to this antigenic peptide domain of *T. cruzi* revealed easily detectable levels of antibodies in greater than 95 percent of *T. cruzi* infected sera samples from several South American countries.

The antigenic peptide domain of *T. cruzi* comprises the amino acid sequence Ala Glu Pro Lys $X_1$ Ala Glu Pro Lys $X_2$ Ala Glu Pro Lys $X_3$ (SEQ ID NO: 3), wherein X is Pro or Ser and when $X_1$ is Set, $X_3$ is Set, or when $X_1$ is Pro, $X_3$ is Pro. The antigenic peptide can also comprise a linker sequence at either the N-terminus or the C-terminus of the antigenic peptide domain wherein the linker sequence facilitates attachment or conjugation of the antigenic peptide domain to various carrier molecules or solid support systems.

The present invention further comprises a method for diagnosing Chagas disease or *T. cruzi* infection by detecting antibodies specific to the inventive antigenic peptide domain. This method comprises contacting a sample of whole blood or an immunoglobulin-containing component of whole blood with the inventive antigenic peptide conjugated to a solid phase, washing unbound antibodies from the solid phase, adding the inventive antigenic peptide conjugated to a detectable moiety to form an antigenic peptide-antibody complex, and detecting the antigenic peptide-antibody complex.

Further still, the present invention comprises a vaccine composition for immunizing an individual for preventing Chagas disease symptoms of *T. cruzi* infection upon exposure to *T. cruzi*. The vaccine composition comprises an immunologically effective amount of the inventive antigenic peptide and a vaccine adjuvant, such as Freund's adjuvant.

BRIEF DESCRIPTION OF THE DRAWINGS

FIG. 1 shows the DNA sequence and deduced amino acid sequence of a 636 base pair TcD insert shown with residues blocked to indicate a 10-amino acid repetitive unit and the number of repeats. Boxed amino acids mark degeneracies in the repeat unit. The DNA sequence and deduced amino acid sequence are also shown in SEQ ID NOs: 1 and 2.

In FIG. 2B the adsorbance values are for 127 T. cruzi infection sera, 9 acute Chagas disease sera, 15 other infected sera, including leishmaniasis, 10 malaria, 16 mycobacterial infection and 32 normal sera. All sera samples were evaluated with synthetic antigenic peptide.

DETAILED DESCRIPTION OF THE INVENTION

Figure 2B:
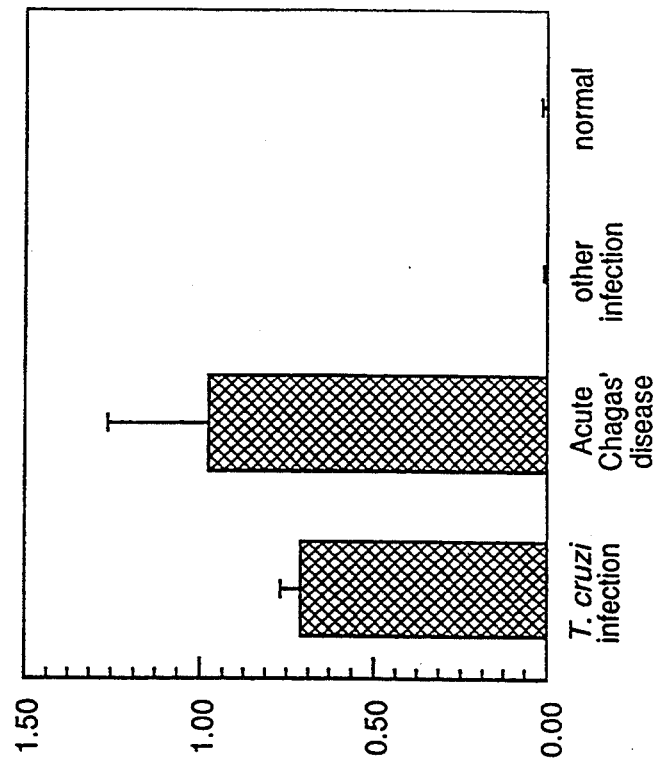
FIGS. 2A and 2B show an ELISA evaluation of recombinant TcD and synthetic TcD peptide. Absorbance values are based upon a population of 127 individuals with T. cruzi infection, 34 individuals with leishmaniasis, 10 with malaria, 17 mycobacterial infections and 32 normal sera, against T. cruzi lysate (hatched bars) and recombinant antigenic peptide (double dash hatched bars).

A major antigenic epitope of an approximately 260 T. cruzi antigen expressed predominantly by trypomastigotes has been identified and synthesized. This antigenic peptide domain of T. cruzi is conserved among geographically diverse T. cruzi isolates. Conservation of the antigen was further indicated by the presence of TcD-specific antibodies in sera from Chagas patients having great clinical and geographical diversity, produced as a result of natural infection with T. cruzi parasites expressing the antigenic peptide repetitive epitope. This antigenic peptide domain of T. cruzi is useful for diagnosing T. cruzi infection, Chagas disease, and for use in a vaccine composition to protect individuals from Chagas disease or other lethal complications upon exposure to T. cruzi parasites.

Response to the antigenic peptide domain of T. cruzi was found to have such extremely high prevalence in seroreactive Chagas patients that it has usefulness as a diagnostic agent. Particularly, the antigenic peptide domain induces antibodies in such patients such that infection by T. cruzi or symptoms of Chagas disease can diagnosed by the presence of such antibodies using an ELISA-type diagnostic assay with recombinant or synthetic antigenic peptide from T. cruzi.

The antigenic peptide domain of T. cruzi comprises the protein sequence Ala Glu Pro Lys XAla Glu Pro Lys $X_2$ Ala Glu Pro Lys $X_3$(SEQ ID NO: 3), wherein X is Pro or Ser and when $X_1$ is Ser, $X_3$ is Ser, or when $X_1$ is Pro, $X_3$ is Pro. The antigenic peptide comprises at least a 15 residue sequence having three groups of five amino acids as a repeat sequence. The antigenic peptide domain can have additional five residue Ala Glu Pro Lys X (SEQ ID NO: 4) sequences to cause the antigenic peptide to be 15, 20, 25, 30, 35, 40, etc., amino acids in length.

Moreover, mice immunized with the inventive antigenic peptide have been protected from lethal T. cruzi infection. Therefore, the inventive antigenic peptide can be used as a vaccine to prevent generalized infection from T. cruzi and enhance the host immune response to T. cruzi exposure.

The present inventive antigenic peptide is the first such antigen having an epitope with serodiagnostic potential. A previously reported cloned T. cruzi antigen (Ibanez et at., Mol. Biochemical Parasitology 25:175, 1987; Ibanez et at., Mol. Biochemical Parasitology 30:27, 1988; and Affranchino et at., Mol. Biochemical Parasitology 34:221, 1989) contained repetitive domains, with one domain reportedly present in an 85 kD antigen Although the 5-amino acid repeat sequence in the 85 kD antigen is similar to the second half of the repeat sequence of the inventive antigenic peptide domain, reactivity with the 85 kD antigen demonstrated only 40% positives in Chagas patient sera. The present inventive peptide, by contrast, exhibited confirmation rates of greater than 95%. This result is consistent with our mapping studies, which indicated that peptides containing only the 5-residue repeat sequence lacked an essential portion of a dominant B-cell epitope of TcD.

In ELISA assay with the synthetic antigenic peptide domain according to the present invention is easy to perform, allows for standardization of reagents, permits screening of large numbers of samples, and can be used with either blood or serum samples.

A series of T. cruzi antigens was purified to find an antigenic peptide domain of a T. cruzi antigen responsible for uniform epitope binding in a vast majority of T. cruzi infected individuals. A genomic expression library was made in λXZAPII with mechanically sheared DNA of T. cruzi. Recombinants expressing T. cruzi antigen genes were selected based upon their reactivity with a pool of Chagas patients' sera, preadsorbed to remove anti-E. coli reactivity. Of twelve clones identified, one clone, called TcD, was exceptionally reactive with the pooled patients' sera. Purified recombinant antigen of clone TcD migrated at about 59 kD on SDS/PAGE. In an immunoblot analysis, the TcD antigen was strongly recognized by pooled Chagas patient sera but not recognized by a pool of normal sera obtained from normal volunteers in Seattle, Wash. Moreover, a pool of high-titer sera from patients with acute visceral leishmaniasis, an infection known to induce antibodies cross-reactive with T. cruzi, was negative for the TcD antigen.

The sequence of the TcD antigen is shown in FIG. 1. Clone TcD encodes a 10-amino acid repetitive sequence. DNA sequence analysis of clone TcD predicted an amino acid sequence comprised entirely of a 10-amino acid repeat sequence arrayed in tandem, and present in 20.5 copies with minor degeneracies in 5 positions (FIG. 1). The predicted molecular weight of recombinant, unglycosylated TcD antigen was 36.3 kD. The migration of the TcD antigen at 59 kD observed during SDS/PAGE most likely reflected a high proline content (28%).

A 636 base pair insert of clone TcD was used to probe Southern blots of T. cruzi DNA and DNA from several other protozoan parasites of humans. The probe hybridized to multiple restriction fragments of T. cruzi DNA but not to the other protozoan parasites including T. brucei, Leishmania chagasi, L. amazonensis, L. donovani, and T. rangeli. Analysis of DNA from seven geographically diverse T. cruzi isolates indicate that TcD gene sequence was conserved among isolates showing restriction fragment link polymorphism and variability in gene-copy number.

The antigenic peptide of T. cruzi comprises at least 15 amino acids having the sequence Ala Glu Pro Lys X Ala Glu Pro X Ala Glu Pro Lys X, wherein X is Pro or Ser. Additional 5 amino acid sequences (Ala Glu Pro Lys X) may be added to the basic 15 residue antigenic peptide domain of T. cruzi. A further sequence may be added to the antigenic peptides to link this peptide at either its N-terminal or C-terminal wherein the linker sequence facilitates attachment or conjugation of the antigenic peptide to carrier molecules. An example of a linker sequence is Gly Cys Gly. The antigenic peptide is made, preferably, by synthetic means on a programmable peptide synthesizer.

ELISA assays have been conducted utilizing antigens or antibodies as the outer components of a sandwich. An ELISA assay of blood or sera from individuals can detect T. cruzi infection of Chagas disease by an antibody specific to the antigenic peptide domain. Therefore, one component of an ELISA sandwich comprises the antigenic peptide of the present invention. Another component comprises an agent that can bind to the anti-*T. cruzi* antibody include, for example, anti-immunoglobulin or protein A. Each component can form a antigenic peptide-antibody complex which contains a detectable moiety. The detectable moiety is known in the art of ELISA diagnostic assays as that component that identifies the antigenic peptide-antibody complex through visual, fluorescent, radionuclide or other means. Common examples of detectable moieties include fluorescent or chemiluminscent agents or enzymes such as horseradish peroxidase.

In a series of studies, patient sera from *T. cruzi* infected individuals or Chagas patients was compared with sera from patients infected with other parasites or normal sera. Patient sera with ELISA values at least five standard deviations greater than mean adsorbance value of normal controls were considered positive. Of confirmed *T. cruzi* infected sera, greater than 95 percent (121 of 127) were positive for an anfi-TcD antibody. Therefore, detection of an anti-TcD antibody in *T. cruzi* infected individuals is a reliable method of detecting Chagas disease or *T. cruzi* infection.

Example 1

This example illustrates cloning of the TcD antigen from *T. cruzi*. A genomic library was constructed in λZAPII (Stratagene) with mechanically sheared DNA of *T. cruzi*. Construction of the library and excision of a pBFK (−) phagemid sequences were performed according to manufacturer's protocols. Recombinants were screened with a pool of Chagas patients' sera preadsorbed to remove anti-*E. coli* reactivity as described in Sambrook et al., *Molecular Cloning: A Laboratory Manual*, Cold Spring Harbor Laboratories, Cold Spring Harbor, N.Y., 1989. A 59 kD recombinant antigen, called clone TcD, was purified from a soluble lysate of induced bacterial cultures by ammonium sulfate fractionation, preparative isoelectric focusing with a Bio-Rad Rotofor IEF cell and 1%–3/10 ampholytes in the presence of 8M urea followed by SDS/PAGE and electroelution as described in Reed et al., *J. Clin. Invest.* 85:690, 1990. Protein concentrations were determined using a Pierce BCA protein assay.

Patients' sera were collected from well-characterized patients with acute or chronic Chagas disease or indeterminant *T. cruzi* infection from the South American countries Brazil (Northern and Southern), Bolivia and Argentina. Normal sera were obtained from individuals living in non-endemic *T. cruzi* areas (Seattle). Sera from confirmed visceral or cutaneous leishmaniasis were obtained from parasitologically confirmed Sudanese patients. Mycobacterial infection sera were obtained from Seattle (tuberculosis) or Haiti for leprosy.

Twelve clones were identified. One clone, called TcD, was exceptionally reactive with patients' sera. Purified recombinant antigen from clone TcD migrated at 59 kD on SDS/PAGE. An immunoblot analysis found that the TcD antigen was strongly recognized by Chagas patients' serum but not recognized by normal sera or by high-titer sera from patients with acute visceral leishmaniasis, an infection known to induce antibodies cross-reactive with *T. cruzi*.

Example 2

Figure 2A:
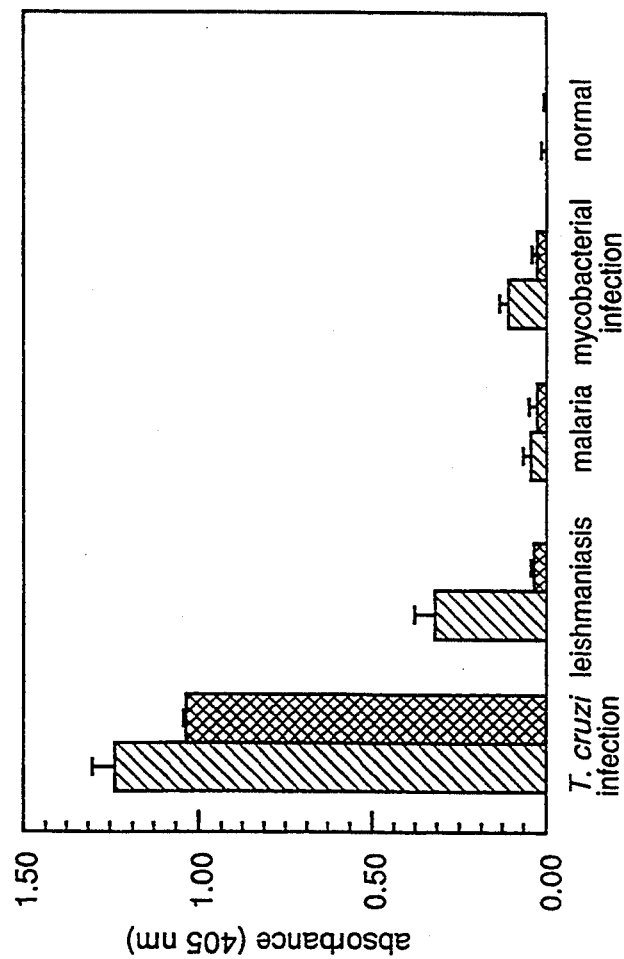

This example illustrates an evaluation of synthetic antigenic peptides derived from the antigenic peptide domain of *T. cruzi* having amino acid length of 5, 10, 15, and 20 amino acids in length. The synthetic peptides were constructed with five amino acid repeat sequences of Ala Glu Pro Lys X, wherein X is Pro or Ser. The data (FIG. 2) show that a peptide containing 15 residues of the repeat sequence was required to map the immunodominant B-cell epitope of TcD. Moreover, the 15 amino acid synthetic peptide had reactivity of patient sera comparable to that obtained with the recombinant molecule. One hundred sixteen of one hundred twenty Chagas sera patients gave positive adsorbance values. In addition, positive TcD-specific antibody responses were detected in 8 of 9 acute Chagas disease patients, indicative of an early immune response to *T. cruzi* infection to this epitope.

Example 3

This example illustrates the usefulness of the inventive antigenic peptide in a vaccine composition to reduce complication and mortality associated with *T. cruzi* infection. A group of 8 week old female C57/6 mice (Jackson Labs, Bar Harbor, Me.) were divided into three treatment groups. Group A (5 mice) was the control group and received no vaccine treatment. Group B was a second control group of 4 mice that received only adjuvant treatment. Group C (4 mice) received the inventive vaccine composition comprising the antigenic peptide (TcD) (15 mer) plus an adjuvant.

The treatment schedule was vaccine administration (s.c.) on day 0, wherein the vaccine comprised 200 μg TcD peptide in complete Freund's adjuvant. Vaccine was administered (i.p.) on day 24 comprising 100 μg TcD. Vaccine was also administered (s.c.) on day 50 wherein this vaccine composition comprised 200 μg TcD peptide in incomplete Freund's adjuvant plus 25 μg muramyl dipeptide (MDP, Calbiochem) an additional adjuvant agent.

At day 57, each mouse was challenged with 1,000 *T. cruzi* (TcTc²) ip. At day 75 (or 18 days post challenge) peak parasitemia was determined and each animal was observed for mortality. The data presented in Table 1 below show the protective effects of the TcD peptide vaccine composition to *T. cruzi* challenge.

TABLE 1

| Group | Treatment | Peak Parasitemia | Mortality |
|---|---|---|---|
| A | nothing | $4 \times 10^5 \pm 5 \times 10^5$ | 5/5 |
| B | adjuvant | $4 \times 10^5 \pm 5 \times 10^5$ | 4/4 |
| C | TcD + adjuvant | $1 \times 10^5 \pm 8 \times 10^4$ | ¼ |

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 636 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v ) ORIGINAL SOURCE:
        ( A ) ORGANISM: Trypanosoma cruzi ( v i i ) IMMEDIATE SOURCE:
        ( B ) CLONE: TcD ( i x ) FEATURE:
        ( A ) NAME/KEY: CDS
        ( B ) LOCATION: 8..628

( x i ) SEQUENCE DESCRIPTION: SEQ ID NO:1:

```
GAATTCA GCA GAG CCC AAA CCA GCG GAG CCG AAG TCA GCA GAG CCT AAA             49
        Ala Glu Pro Lys Pro Ala Glu Pro Lys Ser Ala Glu Pro Lys
         1               5                      10

CCA GCG GAG CCG AAA TCG GCA GAG CCC AAA CCA GCG GAG CCG AAA TCG             97
Pro Ala Glu Pro Lys Ser Ala Glu Pro Lys Pro Ala Glu Pro Lys Ser
 15              20                  25                      30

GCA GAG CCC AAA CCA GCG GAG CCG AAA TCG GCA GGG CCT AAA CCA GCG            145
Ala Glu Pro Lys Pro Ala Glu Pro Lys Ser Ala Gly Pro Lys Pro Ala
             35                  40                      45

GAG CCG AAG TCA GCG GAG CCT AAA CCA GCG GAG CCG AAA TCA GCA GAG            193
Glu Pro Lys Ser Ala Glu Pro Lys Pro Ala Glu Pro Lys Ser Ala Glu
             50                  55                  60

CCC AAA CCA GCG GAG CCG AAA TCG GCA GAG CCC AAA CCA GCG GAG CCG            241
Pro Lys Pro Ala Glu Pro Lys Ser Ala Glu Pro Lys Pro Ala Glu Pro
         65                  70                      75

AAG TCA GCA GAG CCC AAA CCA GCG GAG TCG AAG TCA GCA GAG CCT AAA            289
Lys Ser Ala Glu Pro Lys Pro Ala Glu Ser Lys Ser Ala Glu Pro Lys
     80                      85                      90

CCA GCG GAG CCG AAA TCG GCA GAG CCC AAA CCA GCG GAG TCG AAG TCA            337
Pro Ala Glu Pro Lys Ser Ala Glu Pro Lys Pro Ala Glu Ser Lys Ser
 95                 100                 105                     110

GCA GAG CCC AAA CCA GCG GAG CCG AAG TCA GCA GAG CCC AAA CCA GCG            385
Ala Glu Pro Lys Pro Ala Glu Pro Lys Ser Ala Glu Pro Lys Pro Ala
                 115                 120                     125

GAG CCG AAG TCA GCA GAG CCC AAA CCA GCG GAG CCG AAA TCA GCG GAG            433
Glu Pro Lys Ser Ala Glu Pro Lys Pro Ala Glu Pro Lys Ser Ala Glu
             130                 135                     140

CCC AAA CCA GCG GAG CCG AAA TCA GCA GAG CCC AAA CCA GCG GAG TCG            481
Pro Lys Pro Ala Glu Pro Lys Ser Ala Glu Pro Lys Pro Ala Glu Ser
         145                 150                     155

AAA TCA GCG GGG CCT AAA CCA GCG GAG CCG AAG TCA GCG GAG CCA AAA            529
Lys Ser Ala Gly Pro Lys Pro Ala Glu Pro Lys Ser Ala Glu Pro Lys
     160             165                     170

CCA GCG GAG CCG AAA TCA GCG GAG CCA AAA CCA GCG GAG CCG AAA TCG            577
Pro Ala Glu Pro Lys Ser Ala Glu Pro Lys Pro Ala Glu Pro Lys Ser
 175                 180                     185                 190

GCA GAG CCC AAA CCA GCG GAG CCG AAG TCA GCA GAG CCA AAA CCA GCG            625
Ala Glu Pro Lys Pro Ala Glu Pro Lys Ser Ala Glu Pro Lys Pro Ala
                 195                     200                 205

GAG CCGAATTC                                                              636
Glu
```

( 2 ) INFORMATION FOR SEQ ID NO:2:

( i ) SEQUENCE CHARACTERISTICS:
        ( A ) LENGTH: 207 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ala Glu Pro Lys Pro Ala Glu Pro Lys Ser Ala Glu Pro Lys Pro Ala
 1               5                  10                  15
Glu Pro Lys Ser Ala Glu Pro Lys Pro Ala Glu Pro Lys Ser Ala Glu
             20                  25                  30
Pro Lys Pro Ala Glu Pro Lys Ser Ala Gly Pro Lys Pro Ala Glu Pro
         35                  40                  45
Lys Ser Ala Glu Pro Lys Pro Ala Glu Pro Lys Ser Ala Glu Pro Lys
     50                  55                  60
Pro Ala Glu Pro Lys Ser Ala Glu Pro Lys Pro Ala Glu Pro Lys Ser
 65                  70                  75                  80
Ala Glu Pro Lys Pro Ala Glu Ser Lys Ser Ala Glu Pro Lys Pro Ala
                 85                  90                  95
Glu Pro Lys Ser Ala Glu Pro Lys Pro Ala Glu Ser Lys Ser Ala Glu
             100                 105                 110
Pro Lys Pro Ala Glu Pro Lys Ser Ala Glu Pro Lys Pro Ala Glu Pro
         115                 120                 125
Lys Ser Ala Glu Pro Lys Pro Ala Glu Pro Lys Ser Ala Glu Pro Lys
     130                 135                 140
Pro Ala Glu Pro Lys Ser Ala Glu Pro Lys Pro Ala Glu Ser Lys Ser
145                 150                 155                 160
Ala Gly Pro Lys Pro Ala Glu Pro Lys Ser Ala Glu Pro Lys Pro Ala
                 165                 170                 175
Glu Pro Lys Ser Ala Glu Pro Lys Pro Ala Glu Pro Lys Ser Ala Glu
             180                 185                 190
Pro Lys Pro Ala Glu Pro Lys Ser Ala Glu Pro Lys Pro Ala Glu
         195                 200                 205
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( D ) OTHER INFORMATION: Xaa is Pro or Ser; when Xaa in
        position 5 is Ser, Xaa in position 10 is Pro and Xaa in
        position 15 is Ser; when Xaa in position 5 is Pro, Xaa in
        position 10 is Ser and Xaa in position 15 is Pro.

( x i ) SEQUENCE DESCRIPTION: SEQ ID NO:3:

```
Ala Glu Pro Lys Xaa Ala Glu Pro Lys Xaa Ala Glu Pro Lys Xaa
 1               5                  10                  15
```

( 2 ) INFORMATION FOR SEQ ID NO:4:

( i ) SEQUENCE CHARACTERISTICS:
        ( A ) LENGTH: 5 amino acids
        ( B ) TYPE: amino acid ( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( i x ) FEATURE:
    ( D ) OTHER INFORMATION: Xaa is Pro or Ser.

( x i ) SEQUENCE DESCRIPTION: SEQ ID NO:4:

Ala Glu Pro Lys Xaa
1               5

I claim:

1. A method for detecting antibodies to a 260 Kd antigen present in *Trypanosoma cruzi* comprising:
   (a) obtaining an antibody-containing sample from an individual;
   (b) contacting the sample with a peptide that is a major antigenic epitope of the 260 Kd *T. cruzi* antigen, comprising the amino acid sequence Ala Glu Pro Lys Xaa Ala Glu Pro Lys Xaa Ala Glu Pro Lys Xaa (SEQ ID NO:3), wherein Xaa is Pro or Set and when Xaa in position 5 is Ser, Xaa in position 10 is Pro and Xaa in position 15 is Ser, or when Xaa in position 5 is Pro, Xaa in position 10 is Set and Xaa in position 15 is Pro; and
   (c) detecting the presence of antibodies bound to the peptide.

2. The method of claim 1, wherein the peptide further comprises one or a plurality of Ala Glu Pro Lys Xaa (SEQ ID NO:4) peptide sequences wherein Xaa is Pro or Ser.

3. The method of claim 1, wherein the peptide further comprises a linker sequence at either the N-terminal or the C-terminal, wherein the linker sequence facilitates attachment or conjugation of the peptide to carder molecules.

4. The method of claim 1 wherein the sample is a blood sample.

5. The method of claim 4, comprising the steps of:
   (a) contacting the blood sample with the peptide conjugated to a solid phase, such that *T. cruzi*-specific antibodies that are present in the sample bind to the peptide to from a peptide-antibody complex;
   (b) removing unbound antibodies from the solid phase;
   (c) adding a detection reagent selected from the group consisting of an antiimmunoglobulin that specifically binds to the antibodies present in the sample and Protein A, wherein the detection reagent is conjugated to a detectable moiety, to form a peptide-antibody-detection reagent complex;
   (d) removing unbound detecting reagent from the solid phase; and
   (e) dectecting the peptide-antibody-detecting reagent complex.

6. The method of claim 5, wherein the detectable moiety is a colorometric agent, a fluorescent agent, a chemiluminescent agent or a radionuclide.

7. The method of claim 5, wherein the peptide further comprises one or a plurality of Ala Glu Pro Lys Xaa (SEQ ID NO:4) peptide sequences wherein Xaa is Pro or Ser.

8. The method of claim 5, wherein the peptide further comprises a linker sequence at either the N-terminal or the C-terminal, wherein the linker sequence facilitates attachment or conjugation of the peptide to carder molecules.

9. The method of claim 7, wherein the detectable moiety is a colorometric agent, a fluorescent agent, a chemiluminescent agent or a radionuclide.

10. The method of claim 8, wherein the detectable moiety is a colorometric agent, a fluorescent agent, a chemiluminescent agent or a radionuclide.

11. A kit for evaluating an antibody-containing sample for the presence of antibodies that bind a 260 Kd *T. cruzi* antigen, comprising a peptide comprising the amino acid sequence Ala Glu Pro Lys Xaa Ala Glu Pro Lys Xaa Ala Glu Pro Lys Xaa (SEQ ID NO:3), wherein Xaa is Pro or Ser and when Xaa in position 5 is Ser, Xaa in position 10 is Pro and Xaa in position 15 is Ser, or when Xaa in position 5 is Pro, Xaa in position 10 is Ser and Xaa in position 15 is Pro, and a detection reagent for detecting the *T. cruzi*-specific antibodies.

12. The kit of claim 11, Wherein the peptide further comprises one or a plurality of Ala Glu Pro Lys Xaa (SEQ ID NO:4) peptide sequences wherein Xaa is Pro or Ser.

13. The kit of claim 11, wherein the peptide further comprises a linker sequence at either the N-terminal or the C-terminal, wherein the linker sequence facilitates attachment or conjugation of the peptide to carrier molecules.

* * * * *